United States Patent
Shih et al.

(10) Patent No.: US 9,878,059 B2
(45) Date of Patent: Jan. 30, 2018

(54) TIN SULFIDE QUANTUM DOTS FOR IN VIVO NEAR INFRARED IMAGING

(71) Applicants: Wei-Heng Shih, Bryn Mawr, PA (US); Wan Y. Shih, Bryn Mawr, PA (US); Song Han, Philadelphia, PA (US); Xiaomin Niu, Philadelphia, PA (US); Shi Fang, Philadelphia, PA (US)

(72) Inventors: Wei-Heng Shih, Bryn Mawr, PA (US); Wan Y. Shih, Bryn Mawr, PA (US); Song Han, Philadelphia, PA (US); Xiaomin Niu, Philadelphia, PA (US); Shi Fang, Philadelphia, PA (US)

(73) Assignee: DREXEL UNIVERSITY, Philadelphia, PA (US)

( * ) Notice: Subject to any disclaimer, the term of this patent is extended or adjusted under 35 U.S.C. 154(b) by 0 days.

(21) Appl. No.: 15/092,865

(22) Filed: Apr. 7, 2016

(65) Prior Publication Data

US 2016/0297839 A1    Oct. 13, 2016

Related U.S. Application Data

(60) Provisional application No. 62/144,855, filed on Apr. 8, 2015.

(51) Int. Cl.
| | |
|---|---|
| C07F 7/00 | (2006.01) |
| A61K 49/18 | (2006.01) |
| A61K 49/00 | (2006.01) |
| C09K 11/02 | (2006.01) |
| C09K 11/66 | (2006.01) |
| B82Y 40/00 | (2011.01) |
| B82Y 15/00 | (2011.01) |
| B82Y 30/00 | (2011.01) |

(52) U.S. Cl.
CPC ...... *A61K 49/1836* (2013.01); *A61K 49/0067* (2013.01); *C09K 11/02* (2013.01); *C09K 11/661* (2013.01); *B82Y 15/00* (2013.01); *B82Y 30/00* (2013.01); *B82Y 40/00* (2013.01); *Y10S 977/774* (2013.01); *Y10S 977/896* (2013.01); *Y10S 977/927* (2013.01)

(58) Field of Classification Search
USPC ........................................................ 556/81
See application file for complete search history.

(56) References Cited

U.S. PATENT DOCUMENTS

| 8,652,360 B2 | 2/2014 | Texier-Nogues et al. |
| 2013/0146834 A1 | 6/2013 | Cho et al. |

OTHER PUBLICATIONS

Nair et al., Semicond. Sci. Technol., 1991, 6, 132-134.*
Voitekhovich et al, Chem. Mater., 2008, 20, 4545-4547.*
Xu et al., J. Amer. Chem. Soc., 2009, 131, 15990.*
Kim, Sungjee, et al. "Near-infrared fluorescent type II quantum dots for sentinel lymph node mapping." Nature biotechnology 22.1 (2004): 93-97.
Aswathy, Ravindran Girija, et al. "Near-infrared quantum dots for deep tissue imaging." Analytical and bioanalytical chemistry 397.4 (2010): 1417-1435.
Sohila, S., et al. "Synthesis and characterization of SnS nanosheets through simple chemical route." Materials Letters 65.8 (2011): 1148-1150.
Au, Giang HT, et al. "Assessing breast cancer margins ex vivo using aqueous quantum-dot-molecular probes." International journal of surgical oncology 2012 (2012).
Li, Yan, et al. "In vivo cancer targeting and imaging-guided surgery with near infrared-emitting quantum dot bioconjugates." Theranostics 2.8 (2012): 769-776.
Yan, Xinlong, et al. "Microwave- and conventional-hydrothermal synthesis of CuS, SnS and ZnS: optical properties." Ceramics International 39.5 (2013): 4757-4763.
Liang, Betty Yan Jin, et al. "The influence of reaction temperatures and volume of oleic acid to synthesis SnS nanocrystals by using thermal decomposition method." Thin Solid Films 549 (2013): 159-164.
Oda, Yoshiaki, et al. "Energetic alignment in nontoxic SnS quantum dot-sensitized solar cell employing spiro-OMeTAD as the solid-state electrolyte." Science and Technology of Advanced Materials (2016).
Rath, J. K., et al. "Fabrication of SnS quantum dots for solar-cell applications: Issues of capping and doping." physica status solidi (b) 251.7 (2014): 1309-1321.
Xu, Ying, et al. "Synthesis of SnS quantum dots." Journal of the American Chemical Society 131.44 (2009): 15990-15991.
Grabarek, Zenon, and John Gergely. "Zero-length crosslinking procedure with the use of active esters." Analytical biochemistry 185.1 (1990): 131-135.

* cited by examiner

*Primary Examiner* — Sudhakar Katakam
*Assistant Examiner* — Kofi Adzamli
(74) *Attorney, Agent, or Firm* — Mendelsohn Dunleavy, P.C.

(57) ABSTRACT

An aqueous approach to synthesize capped SnS quantum dots (QDs) followed by optional capping molecule extension by attaching one or more extending molecules to the capping molecule via peptide bond formation at elevated temperature. The capped SnS QDs may have a capping molecule:Sn:S molar ratio of 16:3:1 to 16:12:1. A suspension of SnS QDs was heat-treated at 200° C. for 0.5-4 hrs. The obtained SnS QDs showed an NIR emission peak at 820-835 nm with an excitation wavelength at 690 nm. The as synthesized SnS QDs were found to have high positive zeta potential of ~30 mV and thus were toxic to cells. By neutralizing the SnS QDs the cytotoxicity was reduced to an accepted level. The heat-treatment step can be obviated by adding a glycerol solution containing $S^{2-}$ anions and capping molecule to a glycerol solution of $Sn^{2+}$ ions.

19 Claims, 14 Drawing Sheets
(12 of 14 Drawing Sheet(s) Filed in Color)

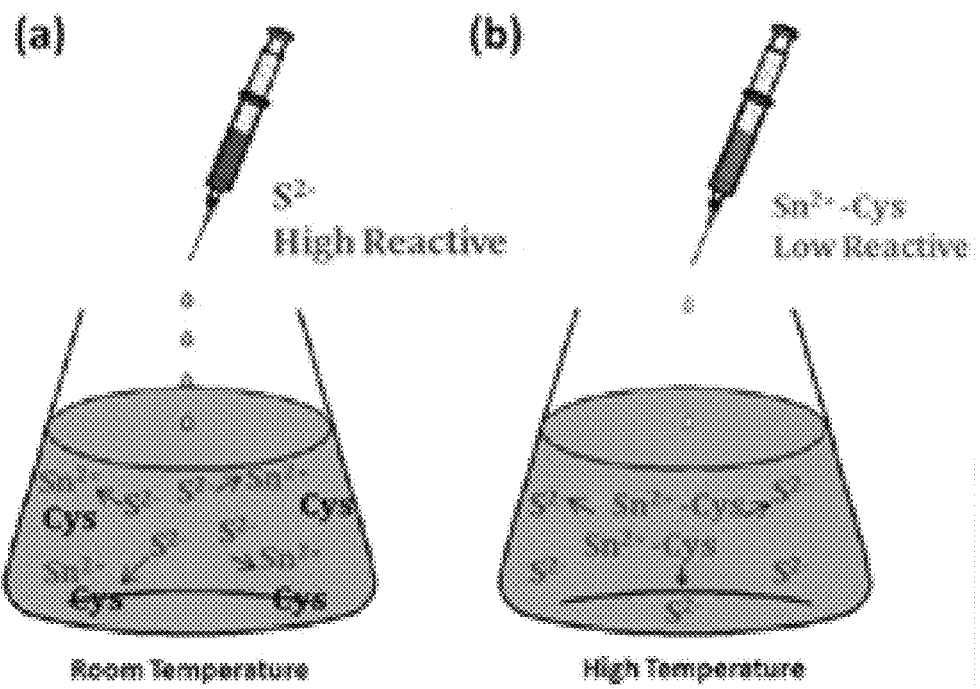
FIGURE 9A                    FIGURE 9B
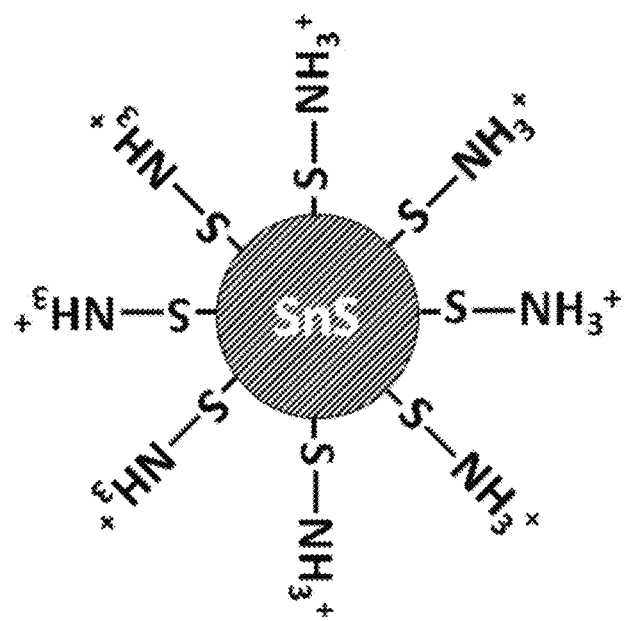
FIGURE 10

US 9,878,059 B2

TIN SULFIDE QUANTUM DOTS FOR IN VIVO NEAR INFRARED IMAGING

RELATED APPLICATION DATA

This application claims priority to U.S. Provisional Application No. 62/144,855, filed Apr. 8, 2015, the entire disclosure of which is hereby incorporated by reference as if set forth fully herein.

BACKGROUND OF THE INVENTION

1. Field of the Invention

The invention relates to the synthesis of stable tin sulfide quantum dots. More specifically, the invention relates to a method for the synthesis of tin sulfide quantum dots which have a relatively low toxicity and photoluminescence properties which render these quantum dots suitable for in vivo near infrared imaging.

2. Brief Description of the State of the Art

Quantum dots (QDs) are semiconductor nanocrystals that have distinctive photoluminescence properties. QDs that emit light in the ultraviolet-visible range have limited penetration in tissues due to the strong absorption of hemoglobin in the mid-visible band. On the other hand, near-infrared (NIR) QDs are suitable for in vivo deep tissue imaging since tissue absorbs only minimal amounts of light in the NIR wavelength range. Furthermore, NIR QDs can be used to avoid tissue auto-fluorescence during imaging. Consequently, NIR quantum dots have attracted much attention in biomedical imaging.

The potential of NIR QDs for biomedical imaging was demonstrated for direct infrared visual guidance throughout a sentinel-lymph-node mapping procedure by minimizing incision and dissection inaccuracies and permitting real-time confirmation of a complete resection. Kim, S., et al., 2003, *Nature biotechnology* 22(1) 93-7. NIR QD bioconjugates have also been utilized to target a tumor in vivo and its margins in mice during image-guided surgery with the benefit of an intraoperative tumor-specific real-time fluorescence-targeted probe. Li, Y., et al., 2012, *Theranostics* 2(8) 769.

NIR QDs for deep tissue imaging, namely, CdTeSe/CdS, InAs/InP/ZnSe, PbS and CdHgTe typically contain heavy metals. Aswathy, R. G., et al., 2010, *Analytical and bioanalytical chemistry* 397(4) 1417-35. In a more recent study, SnS nanosheets were shown to have NIR photoluminescence. Sohila S, et al., 2011, *Materials Letters* 65 1148-50.

As compared to the heavy metal-containing NIR QD's mentioned above, SnS contains relatively low toxicity elements. Sn has a relatively safer minimal risk level (MRL), which is an estimate of daily human exposure to a substance that will not cause an appreciable risk of adverse non-cancer health effects. Toxicological Profile, Agency for Toxic Substances and Disease Registry 2005. As a result, SnS is suitable for use in NIR QDs for in vivo imaging. In recent years, there have been several studies on the synthesis and applications of SnS QDs. In one instance, SnS QDs were synthesized but did not exhibit photoluminescence. Xu, Ying, et al., 2009, *Journal of the American Chemical Society* 131, no. 44 15990-1. Also, the crystallinity of SnS QDs was improved by heat treatment due to Ostwald ripening. Yan, X., et al., 2013, *Ceramics International* 39(5) 4757-63 and Liang, Betty Yan Jin, et al., 2013, *Thin Solid Films* 549 159-64.

SnS QDs have also been shown to be useful for applications in solar cells. Rath, J. K., et al., 2014, *physica status solidi* (b) 251, no. 7 1309-21 and Oda, Yoshiaki, et al., 2014, *Science and Technology of Advanced Materials* 15, no. 3 035006.

It is an object of the present invention to provide a method suitable for synthesis of stable SnS QDs which have a relatively low toxicity and photoluminescence properties suitable for in vivo NIR imaging.

SUMMARY OF THE INVENTION

In one aspect, the present invention relates to a method for the preparation of tin sulfide quantum dots that exhibit a near infrared emission for use in in vivo imaging comprising steps of:

(a) reacting $Sn^{2+}$ cations with $S^{2-}$ anions and a capping molecule in a water-miscible solvent to form capped SnS quantum dots;

(b) optionally extending at least some of the capping moieties of the SnS quantum dots by peptide bond formation to provide extended capped SnS quantum dots; and (c) if necessary, neutralizing the extended capped SnS quantum dots.

The method may be carried out to provide a molar ratio of capping molecule:S in the quantum dots of from about 8:1 to about 32:1 or from about 10:1 to about 20:1 The method may be carried out to provide a molar ratio of Sn:S in the quantum dots of from about 1:1 to about 32:1 or from about 3:1 to about 12:1.

In one embodiment, step (a) of the method includes the steps of:

(i) providing a solution of capping molecule at a pH of from about 1 to about 7 and a temperature of from about 50-90° C.;

(ii) adding a precursor solution containing $Sn^{2+}$ cations while maintaining the temperature at from about 50-90° C. and maintaining the pH at from about 1 to about 7 to provide a mixture; and (ii) adding an aqueous precursor solution containing $S^{2-}$ anions to the mixture while maintaining the temperature at from about 50-90° C. and maintaining the pH at from about 1 to about 7.

The method may further include a step of heat treating the extended capped SnS quantum dots to increase a photoluminescence intensity of the quantum dots and the heat treatment may be carried out at a temperature of from about 180° C. to about 220° C., or from about 190° C. to about 210° C. or at about 200° C. and for a time of from about 0.25 to 5 hrs., or from about 0.5 to 4 hrs., or from about 1 to 3 hrs.

In step (b) of the method extending molecule to capping molecule molar ratio used to extend the capping molecule may be from about 3 to about 30, or from about 5 to about 25 or from about 10 to about 20. 3-mercaptopropionic acid may be employed in step (c) of the method to neutralize the SnS quantum dot.

In an alternative embodiment step (a) of the method includes the following steps:

(i) providing a solution containing $S^{2-}$ ions at a pH of from about 1 to about 7, (ii) adding capping molecules to the solution containing $S^{2-}$ ions in glycerol while maintaining the pH at from about 1 to about 7 to provide a solution containing capping molecules and $S^{2-}$ ions;

(iii) slowly adding a solution containing $Sn^{2+}$ ions at a pH of from about 1 to about 7; to the solution containing capping molecule and $S^{2-}$ ions.

In another aspect, the invention relates to a neutral SnS quantum dot capped with a capping molecule and wherein the capping molecule is extended to provide extending molecule to capping molecule molar ratio used to extend the capping molecule is from about 3 to about 30, or from about 5 to about 25 or from about 10 to about 20. The neutral SnS quantum dot may have a molar ratio of capping molecule:S in the quantum dots of from about 8:1 to about 32:1 or from about 10:1 to about 20:1 The method may be carried out to provide a molar ratio of Sn:S in the quantum dots of from about 1:1 to about 32:1 or from about 3:1 to about 12:1 and 3-mercaptopropionic acid moieties may be attached to the SnS quantum dots.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIGS. 9A-9B illustrate the cation-inverting-injection synthesis method used to increase the PL intensity of the SnS QDs.

FIG. 10 shows a schematic of a Cys-capped SnS QD.

DETAILED DESCRIPTION OF THE PREFERRED EMBODIMENTS

Figure 1A:
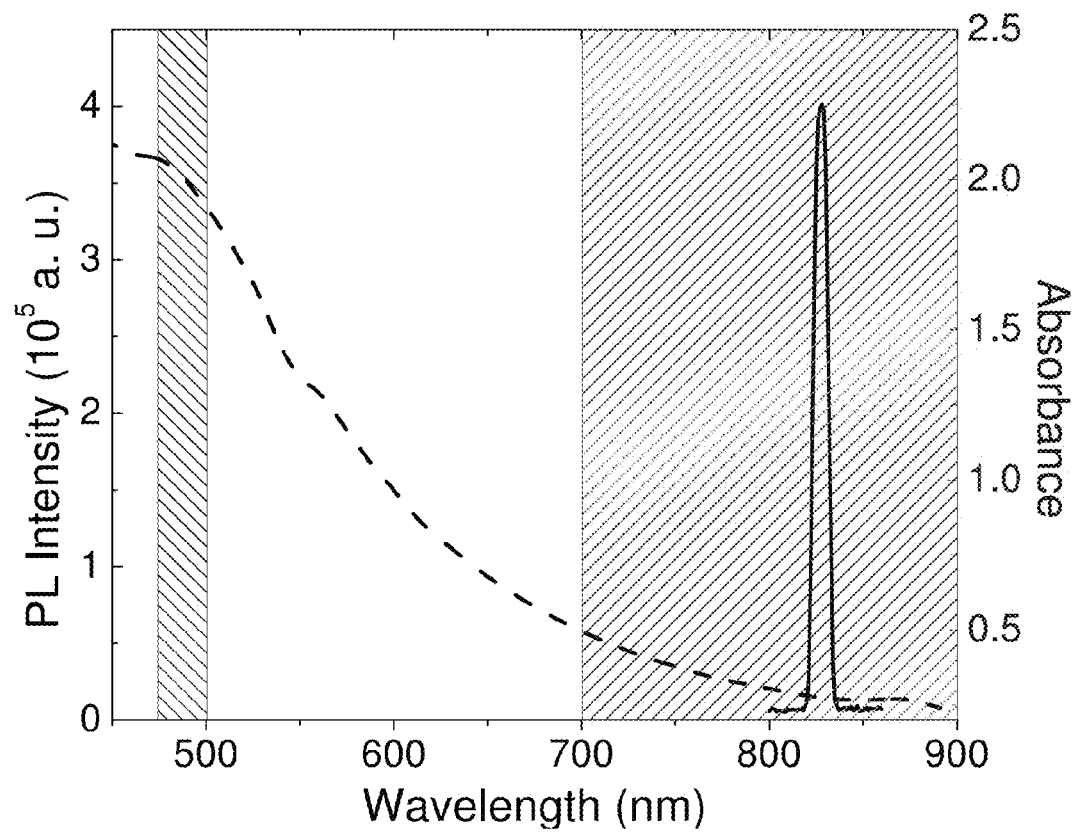
FIG. 1A shows the photoluminescence and UV-absorbance of SnS QD suspensions in glycerol.

For illustrative purposes, the principles of the present invention are described by referencing various exemplary embodiments thereof. Although certain embodiments of the invention are specifically described herein, one of ordinary skill in the art will readily recognize that the same principles are equally applicable to, and can be employed in other apparatuses and methods. Before explaining the disclosed embodiments of the present invention in detail, it is to be understood that the invention is not limited in its application to the details of any particular embodiment shown. The terminology used herein is for the purpose of description and not of limitation. Further, although certain methods are described with reference to certain steps that are presented herein in certain order, in many instances, these steps may be performed in any order as may be appreciated by one skilled in the art, and the methods are not limited to the particular arrangement of steps disclosed herein.

It must be noted that as used herein and in the appended claims, the singular forms "a", "an", and "the" include plural references unless the context clearly dictates otherwise. As well, the terms "a" (or "an"), "one or more" and "at least one" can be used interchangeably herein. It is also to be noted that the terms "comprising", "including", and "having" can be used interchangeably.

In a first aspect, the invention relates to a method for the preparation of tin sulfide (SnS) quantum dots that exhibit a near infrared (NIR) emission and are sufficiently stable and have sufficiently low toxicity for use in in vivo imaging. In the method, SnS QDs are first synthesized in a suitable water-miscible solvent at controlled pH using a suitable capping molecule. Subsequently, the capping molecules of the capped SnS QDs are extended, if necessary, via peptide bond formation. Finally, if necessary, a negatively charged anion is employed to neutralize the capped SnS QDs to provide substantially charge neutral, colloidally stable SnS QDs.

In one embodiment, the capping molecule is first mixed with the tin-containing precursor solution and then the sulfur-containing precursor solution is added thereto. In the initial step of the method, SnS QDs are synthesized in glycerol. A precursor solution containing $Sn^{2+}$ cations in a water-miscible solvent is prepared. Preferably, the selected solvent has a viscosity higher than that of water in order to slow the reaction to produce smaller QDs. Suitable solvents include glycerol, ethylene glycol, water and mixtures thereof, among others. The tin and sulfur salts need to be soluble in the selected solvent. SnCl$_2$ or other suitable sources of Sn$^{2+}$ cations may be used to prepare the initial Sn$^{2+}$ cation solution. Suitable concentrations for the initial Sn$^{2-}$ cation solution range from about 0.001M to about 1M, more preferably, from about 0.005M to about 0.5M and most preferably, from about 0.05M to about 0.1M. Sn$^{2+}$ cations will typically have solubility limits and this may dictate the upper end of the concentration of Sn$^{2+}$ cations in the solution.

A second precursor solution containing S$^{2-}$ anions in water, preferably deionized water, is also prepared. The S$^{2-}$ anion-containing precursor solution may be prepared from Na$_2$S or any other suitable source of S$^{2-}$ anions. Suitable concentrations for the initial S$^{2-}$ anion solution range from about 0.0001M to about 100M, more preferably, from about 0.05M to about 0.5M and most preferably, from about 0.05M to about 0.1M.

The solution of SnS QDs formed by the reaction may have a concentration of SnS QDs of from about 0.01 mM to about 1M, or from about 0.1 mM to about 100 mM or from about 1 to about 10 mM, or about 1.6 mM.

A third solution of capping molecule in the same solvent as the Sn$^{2+}$ cations as discussed above, e.g. glycerol is also prepared. Suitable concentrations for the initial capping molecule solution range from about 0.0001M to about 100M, more preferably, from about 0.05M to about 0.5M and most preferably, from about 0.05M to about 0.1M.

The capping molecule may be any compound that has a group on a first end that is capable of chelating Sn$^{2+}$ cations. One suitable group for this purpose is an —SH group at a first end of the capping molecule to chelate the Sn$^{2+}$ cations and preferably a hydrophilic moiety on the other end of the capping molecule. The hydrophilic moiety provides colloidal stability in the pH range where SnS precipitated from the solution. A preferred capping molecule has a positive charge on the second end of the molecule in order to minimize the potential for cytotoxicity.

Suitable capping molecules are known in the art and include, for example, cysteamine, amino acids with a sulfhydryl group. Suitable capping molecules may be amine salts, fluoride or chloride salts or other salts that readily dissociate in the selected solvent for the reaction. Other possible capping molecules may include mesoporous materials and positively-charged surfactants.

The capping molecule solution is pre-heated to a suitable reaction temperature for the reaction of from about 50° C. to about 90° C., or from about 60° C. to about 80° C., or about 70° C. The first precursor solution containing Sn$^{2+}$ cations is then added while the pH is controlled. The pH is preferably from about 1 to about 12, or from about 2 to about 7, or from about 2.5 to about 5 or about 2.5 to about 4 or about 3. The pH of the solution containing Sn$^{2+}$ cations and capping molecule can be maintained by addition of a suitable base such as tetramethylammonium hydroxide (TMAH) that does not interfere with the reaction. This step of the reaction chelates the capping molecule with the Sn$^{2+}$ cations.

Next, the second precursor solution containing S$^{2-}$ anions in water is added to the capping molecule-Sn$^{2+}$ solution while maintaining it at the reaction temperature given above and a strong acid such as nitric acid that does not interfere with the reaction, is used to maintain the pH in the same ranges as given above. Capped SnS QDs capped precipitated from the reaction mixture.

The molar ratio of capping molecule:Sn:S in the QDs has an effect on the PL intensity of the QDs. Particularly suitable QDs are formed when employing molar ratios of capping molecule:S of from about 8:1 to about 32:1, more preferably, a capping molecule:S molar ratio of from about 10:1 to about 20:1 is employed, and even more preferably the capping molecule:S molar ratio is from about 12:1 to about 18:1 with the best PL intensity being obtained using a capping molecule:S molar ratio of about 16:1. A schematic of a Cys-capped SnS QD is shown in FIG. 10.

Particularly suitable QDs are formed when employing molar ratios of Sn:S of from about 1:1 to about 32:1, more preferably, a Sn:S molar ratio of from about 3:1 to about 20:1 is employed, and even more preferably the Sn:S molar ratio is from about 5:1 to about 10:1 with the best PL intensity being obtained using a Sn:S molar ratio of about 7:1.

In the second optional step of the process, the capping molecule may be lengthened. Lengthening of the capping molecule is an optional step since the initial synthesis step may be carried out with a capping molecule that already has a suitable length in which case the step of extending the capping molecule may not be necessary. The extending molecule should have a carboxyl group at one end that can form a peptide bond. The other end of the extending molecule is preferably hydrophilic, and may preferably also be neutral or negatively charged, though a positively charged extending molecule is also possible since it can be neutralized as described below.

Suitable extending molecules include glycine, amino acids with a sulfhydryl group such as lysine, diacids such as dicarboxylic acids including glutamic acid and aspartic acid and cysteamine (Cys). In one embodiment, by linking glycine with the capping molecule, for example, Cys using, for example, a combination of (1-Ethyl-3-[3-dimethylaminopropyl]carbodiimide hydrochloride (EDC) and (2-(N-morpholino)ethanesulfonic acid (NHS), or EDC alone, as the linker. The carboxyl group on glycine reacts with EDC forming an amine-reactive O-acylisourea intermediate. This intermediate reacts with the amine group on cysteamine, yielding a conjugate of the two molecules joined by a stable amide bond, thereby increasing the length of the capping molecule by the two carbon chains of glycine and EDC. The extending step is typically carried out by formation of a peptide bond.

The extending step is carried out in a suitable solvent such as water, glycerol, or ethylene glycol or any water soluble solvent at pH around 7 or between 6 and 8 such as controlled by an 2-(N-morpholino)ethanesulfonic acid (MES) buffer. The solve may be water, glycerol, ethylene glycol or any mixture thereof. To control the pH at about 7, phosphate buffer saline (PBS) solution, borate buffer solution, and/or MES can be used.

The pH of the solution was raised to from about 5 to about 9, or from about 6 to about 8 or about 7 in order to carry out the extending reaction. pH adjustment can be accomplished using any suitable base that does not interfere with the reaction, such as TMAH. The extending step may preferably be carried out by reacting the EDC, glycine and Cys-capped SnS QDs. In one embodiment, the EDC and NHS solutions in MES are mixed and a glycine solution is added at a suitable temperature of from about 10-40° C., or about 20-30° C. or about 25° C. The pH of the solution is maintained at about the starting pH using a suitable buffer solution such a borate buffer solution. Excess NHS, EDC and glycine are removed by filtration, e.g. microcentrifugation under suitable conditions. After repeating this step several times, multiple glycine extending molecules were conjugated to the surface of each QD thereby extending the capping molecule. A schematic of this reaction is shown below.

Schematic of glycine extending on SnS QDs with the EDC/NHS reaction

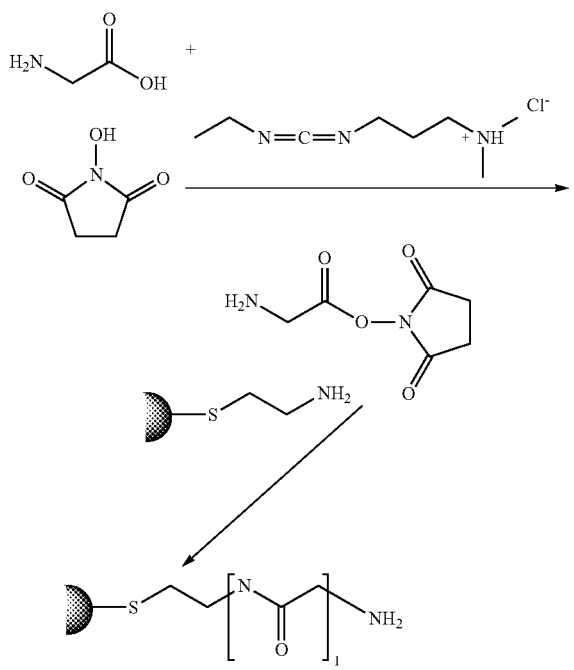

A schematic showing the result of multiple extending reactions is shown below.

Schematic of multiple extending reactions

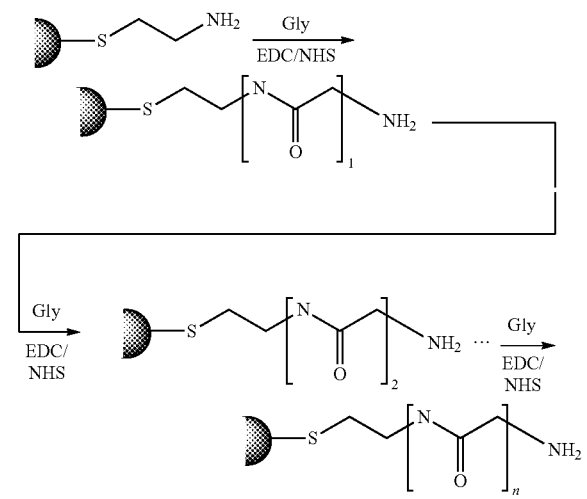

The glycine (Gly):Cys molar ratio used to lengthen the capping molecule may be from about 3 to about 30, or from about 5 to about 25 or from about 10 to about 20.

After stabilization of the SnS QDs by extending the capping molecules as discussed above, hydrothermal treatment was needed to improve the PL intensity. However, for the hydrothermal treatment, the large amount of water added during the extending process has to be replaced by solvent exchange with glycerol to avoid the limitation of boiling of water at 100 t. It is necessary, for example, to increase the percentage of glycerol from 60% to 99% before hydrothermal treatment.

Solvent replacement was carried out by several rounds of centrifugation at, for example, 12,000 rpm for 5 minutes each. At the end of each centrifugation, glycerol was added to the retentate to bring the concentration of the SnS in the suspension to, for example, about 1.6 mM, as measured by the molecular concentration of sulfur. The process was finished when the remaining buffer amount was less than 0.5%. The amount of glycerol in the solvent was increased from 60% to 99%. The SnS suspension was transferred into hydrothermal vessel for hydrothermal heat treatment.

The SnS suspension in about 99% glycerol may then be heat-treated at from about 180° C. to about 220° C., or from about 190° C. to about 210° C., or at about 200° C., for from about 0.25 to 5 hrs., or from about 0.5 to 4 hrs., or from about 1 to 3 hrs. to increase the PL intensity. The obtained SnS QDs showed an NIR emission peak at 820-835 nm with an excitation wavelength at 690 nm. X-ray diffraction indicated that the SnS QDs contain mixtures of the orthorhombic and the zinc blende structures. Use of ethylene glycol and glycerol as the solvent improved the colloidal stability while retaining the crystallinity. The as synthesized SnS QDs were found to have high positive zeta potential of ~30 mV and were toxic to cells thus requiring neutralization.

Since the solvent replacement steps are time-consuming and difficult due to the high viscosity of glyerol, an alternative process was developed to eliminate the need for the solvent replacement steps. To avoid the tedious solvent exchange process and subsequent hydrothermal treatment with low yield, a cation-inverting-injection synthesis method may be employed to improve the PL intensity of the SnS QDs. It is believed that the cation-inverting-injection increases the edge-state emission and suppresses the trap-state emission. Also the lower cation concentration that results in this method allows more anions to participate in the growth of the QDs. As shown in FIGS. 9A-9B, use of a low Sn concentration during the gradual addition of the $Sn^{2+}$ ions leads to the formation of only a few SnS nuclei, leaving most of the $S^{2-}$ ions available for QD growth.

The cation-inverting injection method replaces the initial reaction of the $Sn^{2+}$ ions, the $S^{2+}$ ions and capping molecule described above, and thus is carried out prior to the step of extending the capping molecule. In the cation-inverting-injection process of FIG. 9A, $S^{2-}$ ions are added into glycerol, the pH is adjusted to from about 1 to about 5, or from about 2 to about 4 or from about 2.5 to about 3.5 or to about 3 and then capping molecule (Cys) was added. In the process of FIG. 9B $Sn^{2+}$ ions and cysteamine are added at pH 3, the pH having been adjusted using a suitable acid such as nitric acid. After 10 minutes, the solution of FIG. 9B was slowly pumped into the solution of FIG. 9A. An exemplary Cys-capped SnS QD is shown schematically in FIG. 10.

Figure 11:
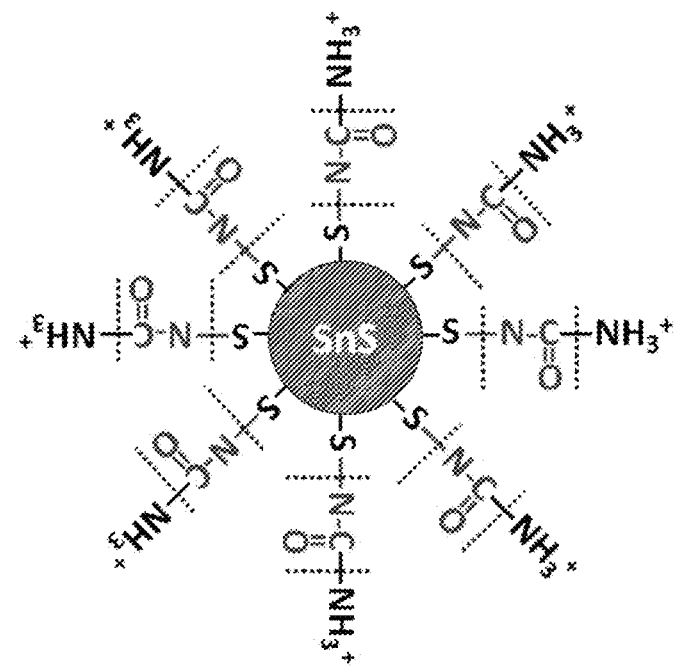
FIG. 11 is a schematic of the Cys-capped SnS QD of FIG. 10 extended with glycine.

It was found that this cation-inverting-injection synthesis method significantly increased the PL intensity, without the need for heat treatment. Further, extending of the capping molecules of these SnS QDs using glycine, as described above, provided an SNS QD suspension that was stable for at least one week at pH 6.5. A schematic representation of a Cys-capped SnS QD extended with glycine is shown in FIG. 11.

Figure 12:
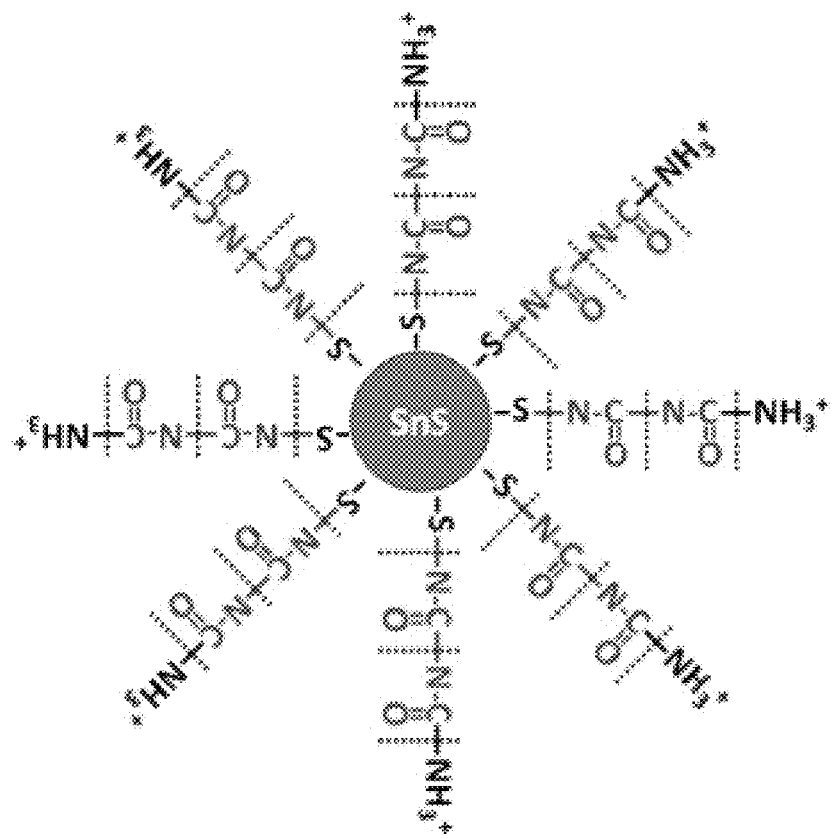
FIG. 12 is a schematic of the glycine-extended Cys-capped the SnS QDs neutralized by 3-mercaptopropionic acid linked the capping molecules.

Since positively charged QDs may be cytotoxic, the final step of the process is to neutralize the SnS QDs. To further modify the QD surface and reduce the positive charge, a negatively charged capping molecule preferably having a hydrophilic tail and a negative charge on the other end. Suitable negatively charged capping molecules include 3-mercaptopropionic acid (MPA), which has a negatively charged carboxyl group, may be attached to the amine group(s) on QDs surface by electrostatic interaction. 11-mercaptoundecanoic acid, 6-mercaptohexanoic acid, glutamic acid and aspartic acid may also be used. A suitable amount of the negatively charged capping molecule is added to SnS suspension to substantially neutralize or neutralize the charge on the SnS QDs. Glycine-extended Cys-capped the SnS QDs that have been neutralized by 3-mercaptopropionic acid linked capping molecules is shown schematically in FIG. 12.

In a second aspect, the present invention relates to SnS QDs made by the method of the present invention. The SnS QDs of the present invention are neutralized SnS QDs having a low cytotoxicity, a high PL intensity near infrared emission and a good storage stability. The neutralized SnS QDs are capped to provide QDs having a molar ratio of capping molecule:Sn:S of from about 16:4:1 to about 16:10:1 is employed, and even more preferably the capping molecule:Sn:S molar ratio is from about 16:6:1 to about 16:8:1 with the best PL intensity being obtained using a capping molecule:Sn:S molar ratio of about 16:7:1 with Cys as the capping molecule.

The SnS QDs of the invention have extended capping molecules. The extended capped SnS QDs of the invention may include glycine linked to the amino group of the capping molecule via a linker formed from EDC and NHS as shown in the schematics of the extending reactions given above. The extending molecule:capping molecule molar ratio used to lengthen the capping molecule may be from about 3 to about 30, or from about 5 to about 25 or from about 10 to about 20.

The neutralized SnS QDs may have an anion such as MPA attached to the lengthened capping molecule by, for example, electrostatic interaction in order to neutralize or substantially neutralize the SnS QDs.

The invention will be further illustrated by the following non-limiting examples.

Example 1

Synthesis of SnS Quantum Dots

Tin (II) chloride, $SnCl_2$, (Sigma Aldrich) and sodium sulfide, $Na_2S$, (Sigma Aldrich) were used as the initial reactants for the synthesis. A 0.08 M $SnCl_2$ precursor solution in glycerol (Sigma Aldrich) was prepared by dissolving 7.58 g of $SnCl_2$ in 50 mL of glycerol. A 0.08 M $Na_2S$ precursor solution in water was prepared by dissolving 3.12 g of $Na_2S$ in 50 mL of deionized (DI) water. Cysteamine (Cys) (Sigma Aldrich) was used as the capping molecule.

First, 0.55 g Cys was added in 15 ml of glycerol to achieve a 0.32 M solution and the pH was adjusted to 3 by adding nitric acid (Fisher Scientific) and the solution was heated at 70° C. for 10 min., followed by the addition of 1 ml of the 0.08 M $SnCl_2$ precursor solution at 70° C. while maintaining the pH at 3 by adding tetramethylammonium hydroxide (TMAH) (Fisher Scientific) in order to chelate the Cys with $Sn^{2+}$. This step was followed by adding 1 ml of the $Na_2S$ precursor solution to the mixture at 70° C. while the pH was maintained at 3 by adding nitric acid and then stirring for 10 min. This procedure provided SnS QDs having a Cys:Sn:S molar ratio of 16:1:1.

In order to determine the effect of the Cys:Sn:S molar ratio on the photoluminescence (PL) intensity and the stability of the precipitated SnS QDs, the suspension was stirred for 10 minutes, and various amounts of excess $SnCl_2$ precursor solution in glycerol were added. It was found that the provision of additional Sn in the QDs improved the PL intensity. The final nominal QD concentration was 1.6 mM, based on the concentration of sulfur. It was found that a ratio of Cys:Sn:S of 16:7:1 provided the best PL intensity and thus, QDs synthesized with this ratio were used in the examples described below.

Example 2

Extending of the Capping Molecule on SnS Quantum Dots

To further stabilize the QD suspension, the length of the capping molecule attached to the surface of SnS QDs was increased by linking glycine (Gly) with Cys using 1-Ethyl-3-[3-dimethylaminopropyl]carbodiimide hydrochloride (EDC), (Pierce Biotechnology) and N-hydroxysulfosuccinimide (NHS), Pierce Biotechnology using the reaction described in Grabarek, Z. and Gergely, J., 1990, Zero-length crosslinking procedure with the use of active esters. Anal Biochem 185:131-5. The carboxyl group on the glycine reacted with EDC forming an amine-reactive O-acylisourea intermediate. This intermediate reacted with the amine group on cysteamine, yielding a conjugate of the two molecules joined by a stable amide bond, and, as a result, the length of the capping molecule was increased by two carbon chains.

To carry out this procedure, 5 mg/mL stock solutions of EDC and NHS were made by dissolving 2.5 mg of EDC and NHS, respectively, in 500 μL of 0.1 M 2-(N-morpholino) ethanesulfonic acid (MES), (Fisher Scientific) buffer solution. The pH of 2 ml of a SnS suspension was raised to 7 by adding TMAH, followed by the addition of 500 μL of EDC and 500 μL of NHS at room temperature for 10 min, followed by the addition of 500 μL of 0.5 M freshly prepared glycine solution and this mixture was incubated for 10 min. in order to lengthen the capping molecules. The freshly prepared glycine solution was prepared in 0.1 M MES buffer. The pH of the suspension was kept at 7 by adding an appropriate amount of a 0.1 M borate buffer solution (Fisher Scientific). Excess EDC, NHS and glycine were filtered three times by microcentrifugation (Fisher Scientific) at 10,000 rpm with a 10 kDa filter (Thermo Scientific) for 5 min.

After repeating these steps several times, multiple glycine groups were conjugated to the surface of the QDs' to thereby increase the length of the capping molecule. Different amounts of glycine were added to the QD suspension to conjugate with Cys, and thereby QDs with various Gly:Cys ratios (i.e. 3, 5, 10, 20, 25, and 30) were prepared and studied. This was followed by solvent replacement by several rounds of centrifugation at 12,000 rpm for 5 min. At the end of each round of centrifugation, glycerol was added to the retentate to adjust the concentration of the SnS suspension to 1.6 mM, as determined based on the molecular concentration of sulfur.

Example 3

Solvent Exchange and Heat Treatment

Before heat treatment, solvent exchange was carried out on the SnS suspension to remove excess buffer by centrifugation. The suspension was microcentrifuged at 10,000 rpm for 5 min. with a 10 kDa filter. The retentate was diluted to the original volume with glycerol. The suspension was then centrifuged at 12,000 rpm for 5 min. with a 10 kDa filter and the retentate was diluted to the original volume with glycerol. As the amount of glycerol in the suspension increased as a result of each round of filtration and dilution, the centrifugation time was gradually increased. The remaining amount of buffer was estimated by multiplying the volume ratio of the volume of retentate to the original volume prior to centrifugation, for each round of centrifugation. The process was stopped when the remaining buffer amount was less than 0.5% by volume. The SnS suspension was then transferred into a hydrothermal vessel for heat treatment.

Heat Treatment

The SnS suspension in about 99% glycerol was heat-treated at 200° C. for 0.5, 1, 2, or 4 hrs. The obtained SnS QDs showed an NIR emission peak at 820-835 nm with an excitation wavelength at 690 nm. X-ray diffraction indicated that the SnS QDs contain mixtures of the orthorhombic and the zinc blende structures. The longer treatment time at 200° C. in water improved the crystallinity but reduced the colloidal stability of the QDs. Changing the solvent from water to ethylene glycol and glycerol improved the colloidal stability while retaining the crystallinity. The crystallite sizes of the SnS QDs made in ethylene glycol and glycerol as estimated from the x-ray diffraction peak widths using the Scherrer formula were 8.5 nm to 3.6 nm, respectively. In addition, due to the higher viscosity of glycerol, the colloidal stability of SnS QDs made in glycerol was also enhanced. The as synthesized SnS QDs were found to have high positive zeta potential of ~30 mV and were toxic to cells.

Neutralizing the Positive Surface Change

Positively charged SnS QDs were found to be cytotoxic. Thus, the SnS QDs were neutralized to modify the surface and reduce the positive charge. 3-mercaptopropionic acid (MPA), which has a negatively charged carboxyl group, was attached to the amine group on the surface of the SnS QDs by electrostatic interaction. Various amounts of MPA were added to a SnS suspension to determine the effect of surface charge on the stability of the QDs. (Charges versus MPA/Cys are also shown in the schematic).

Example 4

Cell Culture and Cytotoxicity Test

NIH 3T3 (ATCC) is a mouse embryo fibroblast cell line which is used as a model mammalian cell line for cytotoxicity study of the SnS QDs. 3T3 was cultured with Dulbecco's modified Eagle's medium (DMEM). The cell culture media contained 10% fetal bovine serum (FBS) and 1% penicillin-streptomycin. Cells were incubated at 37° C. in a humidified atmosphere with 5% $CO_2$. When the cells reached 80% confluence, they were seeded into 96 well plates with 5,000 cells/well and cultured with 150 μl media. After 24 hours of incubation, the old media was replaced with media containing various concentrations of SnS QDs. The tested concentrations were 10, 50, 100, 250, 500, 750 and 1000 μM. Cells cultured under identical conditions without addition of QDs were employed as a control. Each sample was prepared triplicate. After 24 hours incubation with different concentration of QDs, the media was removed and the wells were washed three times with 150 μl PBS. An MTS (3-(4,5-dimethylthiazol-2-yl)-5-(3-carboxymethoxyphenyl)-2-(4-sulfophenyl)-2H-tetrazolium) assay was used to assess the metabolic activity. The 96 well plates were incubated for 3 hours after the addition of MTS into each well. The absorbance of each well was measured at a wavelength of 490 nm. The same procedure was repeated after 48 and 72 hours of incubation. The ratio comparing the absorbance of the control and the experimental concentration of the QDs was calculated and used indicate the percentage of cell viability.

Example 5

Immunofluorescent Staining

The HT29 (ATCC) colon cancer cell line was used for this study. With amine-capped QDs, the carboxyl group of streptavidin (SA) was covalently bonded to the amine group through EDC and sulfo-NHS. The SA-QD conjugate was then used to detect the Tn antigen on HT29 cells by immunofluorescent staining. The HT 29 cells were first incubated with 10% goat normal serum, streptavidin, and biotin, respectively, for blocking non-specific binding. For detection, the primary antibody (mouse anti-Tn antigen) was then attached to the Tn antigen on the cell membrane, followed by a biotinylated secondary antibody (goat anti-mouse), which created a binding site for the SA-QD conjugates. After incubation with the SA-QD conjugates for 30 minutes, the cell nuclei were stained with DAPI mounting medium. The HT29 cells were examined under a fluorescent microscope to evaluate Tn antigen detection.

Example 6

Characterization of QDs

The photoluminescence (PL) spectra were obtained using a spectrofluorometer (QuantaMaster 40, PTI, Birmingham, N.J.). The particle hydrodynamic size and zeta potentials were measured using a Malvern zetasizer (Nano S90, Malvern, Worcestershire, UK). The x-ray diffraction patterns of the QDs were examined using a Rigaku SmartLab x-ray diffractometer. The absorption spectra were measured using a UV-vis spectrometer (USB4000, Ocean Optics, FL). The absorption of the SnS QDs for quantum yield analysis was measured using a Tecan microplate reader (Infinite 200 PRO, Männedorf, Switzerland). The fluorescence images of the QDs were examined using an Olympus BX51 microscope with a NIR CCD camera (MicroVista, Intevac, Calif.) including the filters information from Chroma.

Figure 1B:
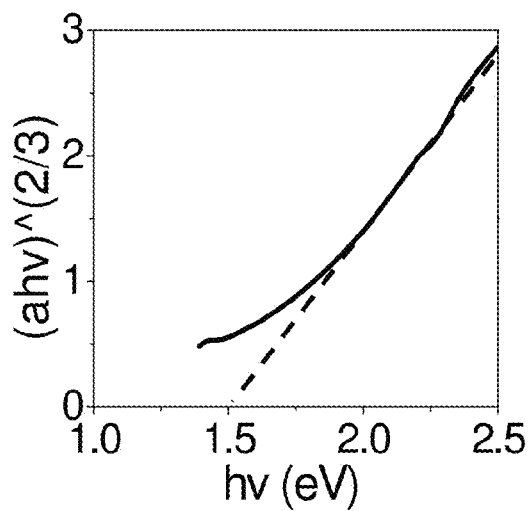
FIG. 1B shows a band gap of about 1.5 eV (827 nm) for the UV-absorbance of FIG. 1A, as estimated using the Tauc equation.

FIG. 1A shows the photoluminescence and UV absorbance of the SnS QD suspensions in glycerol and treated at 200° C. for 4 hours. The SnS QDs showed photoluminescence in the near infrared range with a peak around 830 nm when excited with light of 690 nm wavelength. The synthesized QDs showed UV-vis absorbance in the range of 300-700 nm. The shaded region at around 500 nm in FIG. 1A denotes the excitation window and the shaded region above 700 nm denotes the emission window of the Chroma filters used during immunofluorescent imaging. The band gap of the SnS QDs was estimated using the Tauc equation by taking as the x-intercept of the dashed line in the FIG. 1B at 1.6 eV (775 nm). J. Tauc, R. Grigorovici and A. Vancu 1966 *Phys. Status Solidi* 15 627. The estimated band gap shows a blue shift of 0.3 eV compared to the bulk SnS. This may be due to the quantum confinement of charge carriers in the QDs.

Figure 2:
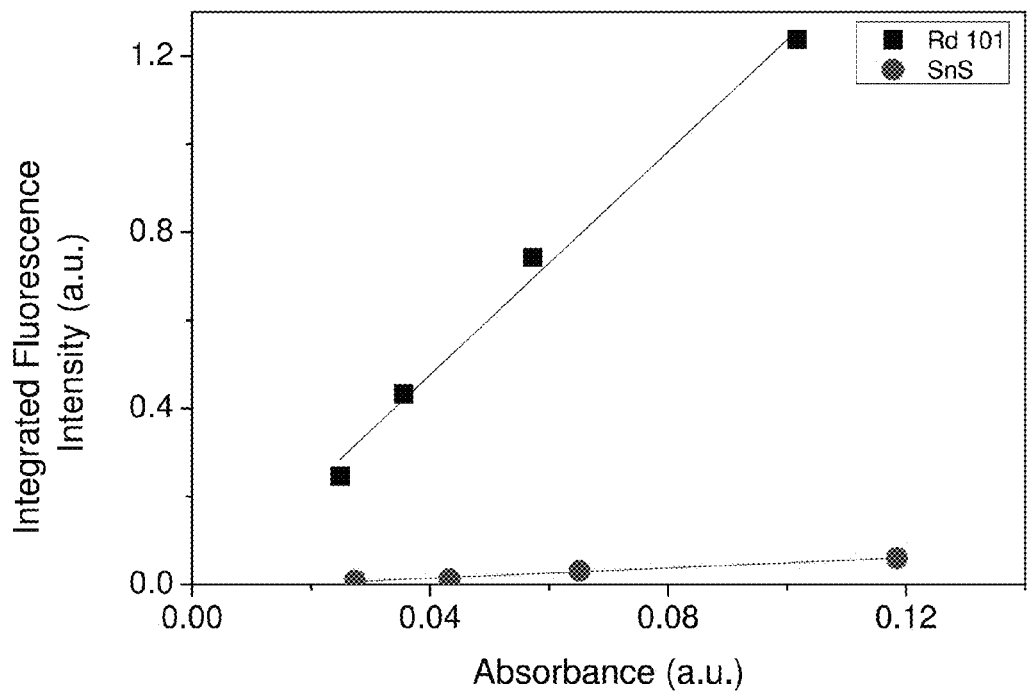
FIG. 2 shows that the quantum yield (QY) of SnS QDs is about 6% using Rhodamine 101 (Rd 101) as a standard.

To measure the quantum yield (QY) of the QDs, Rhodamine 101 (RD 101) (Fisher Scientific, Fairlawn, N.J.) was used as the standard. The absorption of the diluted RD 101 solutions and QD suspensions were measured with the Tecan. The emission spectra were measured with the PTI. The integrated emission intensity was then plotted versus the absorption for both the RD 101 and the QDs as shown in FIG. 2. The quantum yield (QY) of the QDs was obtained by dividing the slope of the SnS line by the slope of the RD 101 line. The QY of RD 101 was taken as 100%. The QY of the SnS QDs was determined to be about 6%.

Figure 3A:
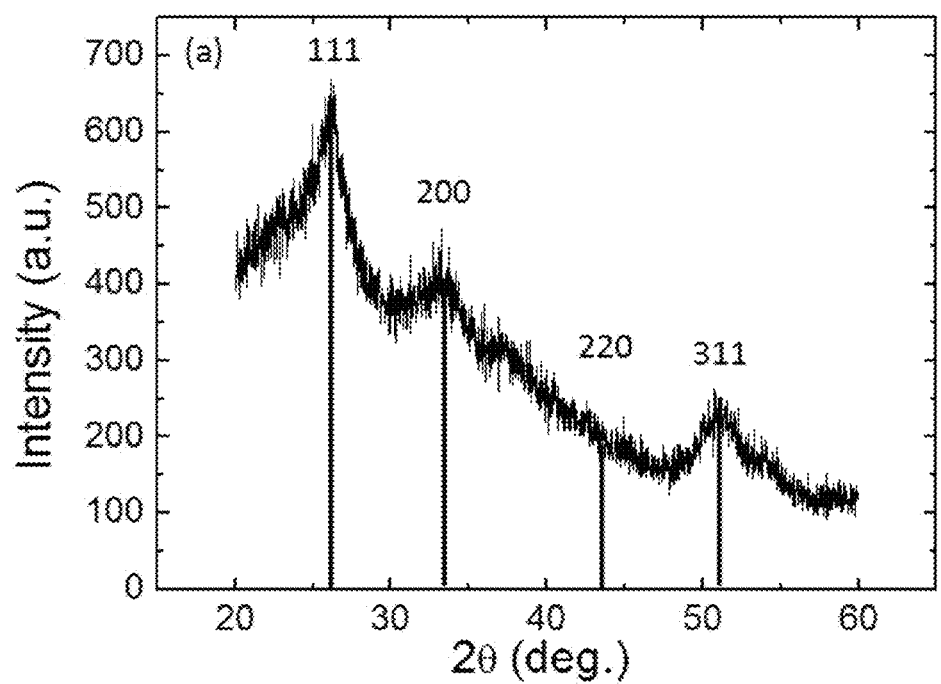
FIG. 3A is the x-ray diffraction pattern (XRD) of SnS QDs in glycerol.
Figure 3B:
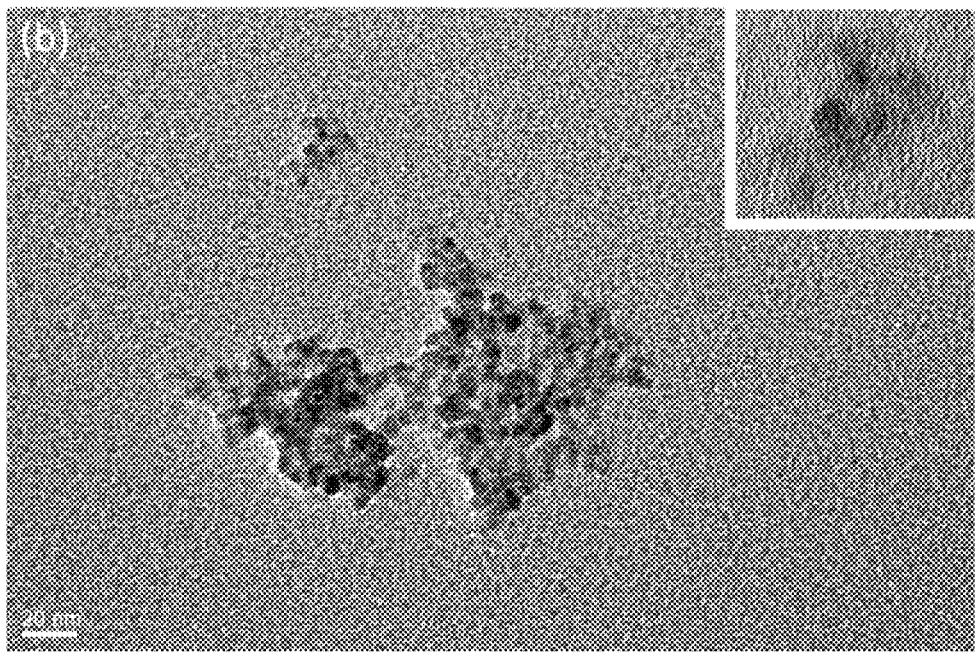
FIGS. 3B-3C are transmission electronic microscope (TEM) images of the SnS QDs before heat treatment and after heat treatment respectively, with high-resolution images shown in the insets.
Figure 3C:
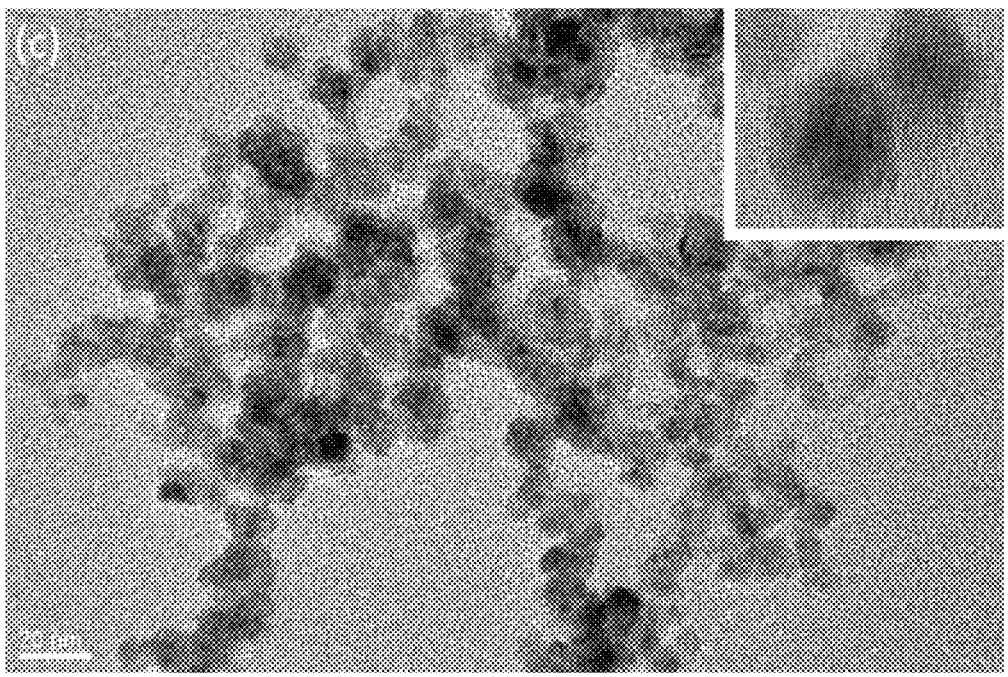

FIG. 3A shows the x-ray diffraction pattern of the SnS powders collected by precipitating the suspensions by adding acetone. It is shown that the SnS QDs have a cubic zinc blende structure. The crystallite size of the SnS QDs, estimated from the XRD peak (111) width in FIG. 3A using the Scherrer formula, was 3.6 nm. TEM images of SnS QDs before and after the heat treatment are shown in FIG. 3B-3C with high-resolution images in the insets, indicating particle size increases and improved crystallinity after heat treatment.

It was found that these SnS QD suspensions were stable for a few hours. To increase the stability, the capping molecules were lengthened to prevent agglomeration. Different amounts of glycine (Gly) were linked to the QD surface, followed by MPA modification to neutralize the surface charge, as shown in Table 1 below.

TABLE 1

SnS QD swith different Gly:Cys Ratios and their sizes

| n | Gly:Cys ratio | Average size (nm) |
|---|---|---|
| 0 | 0 | 16.5 |
| 1 | 10 | 18.6 |
| 2 | 20 | 19.7 |
| 3 | 30 | 21.1 |
| 4 | 40 | 22.4 |

Figure 4:
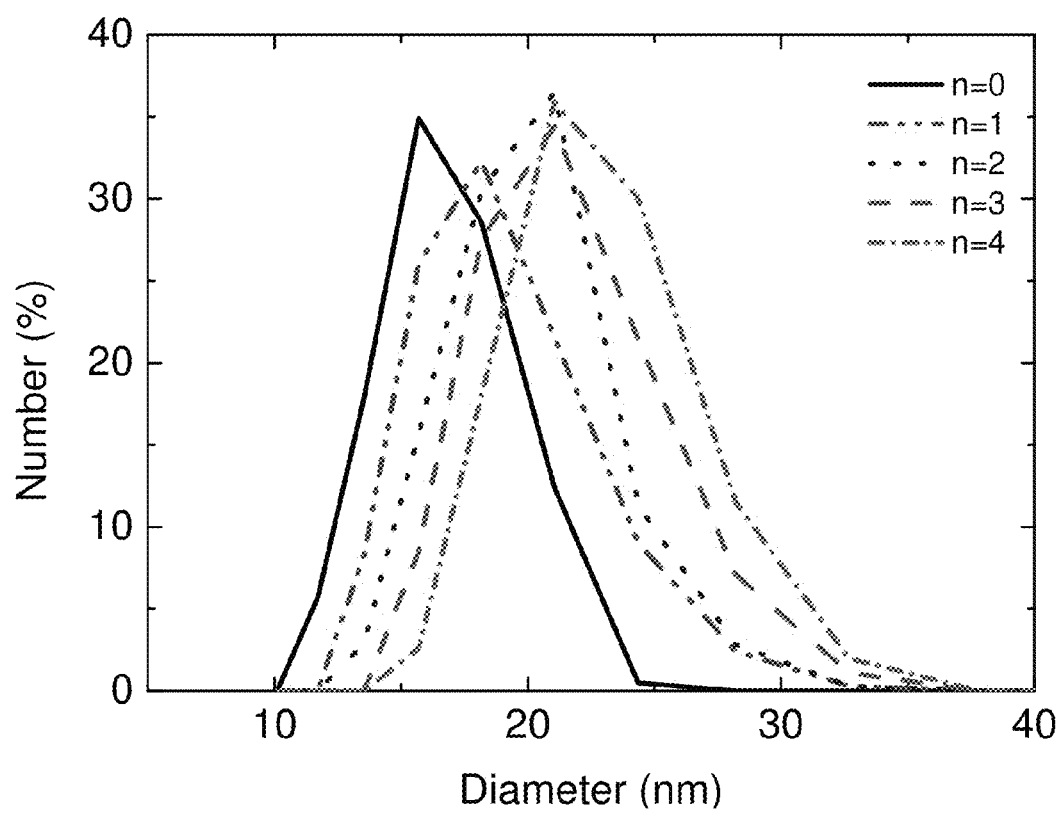
FIG. 4 shows the size and stability of SnS QDs after reacting with different amounts of glycine.
Figure 16:
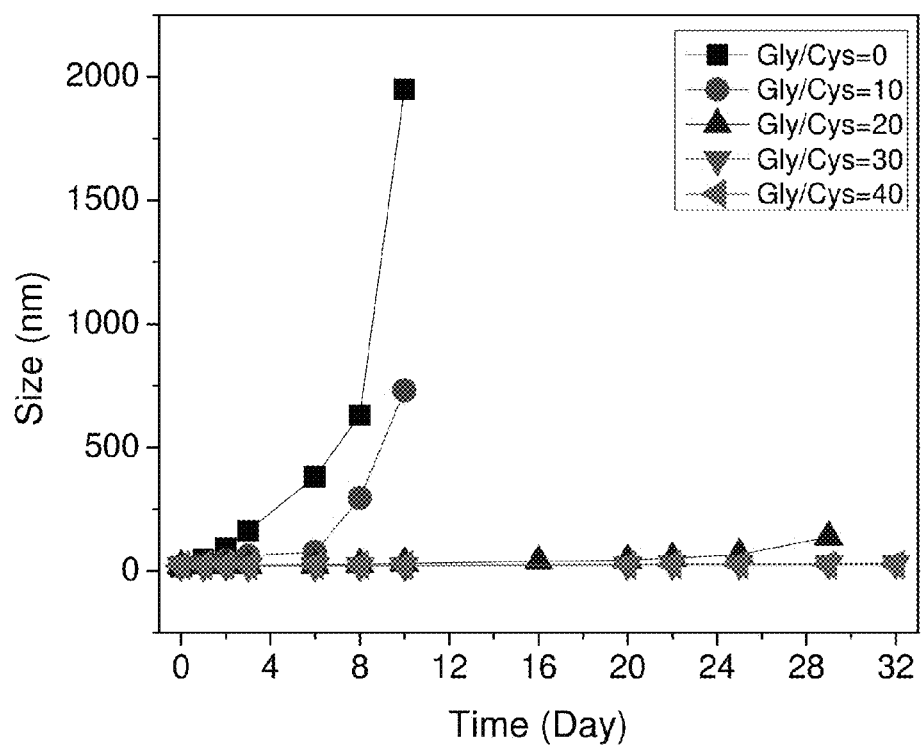
FIG. 16 shows aggregation of SnS QDs over time as described in Example 6.

As shown in FIG. 4, the size of the QDs is increased by 5.9 nm, As determined by comparing a Gly:Cys ratio of 0 with that of 40. The larger size is due to more glycine conjugation on the surface. By monitoring the change of particle size with time it was shown that when the Gly:Cys ratio is higher than 20, the QDs are stable for over 20 days as shown in FIG. 16. With the Gly:Cys ratios at 0 or 10, the QDs aggregated starting at 2 or 6 days respectively, as shown in FIG. 16.

Figure 5A:
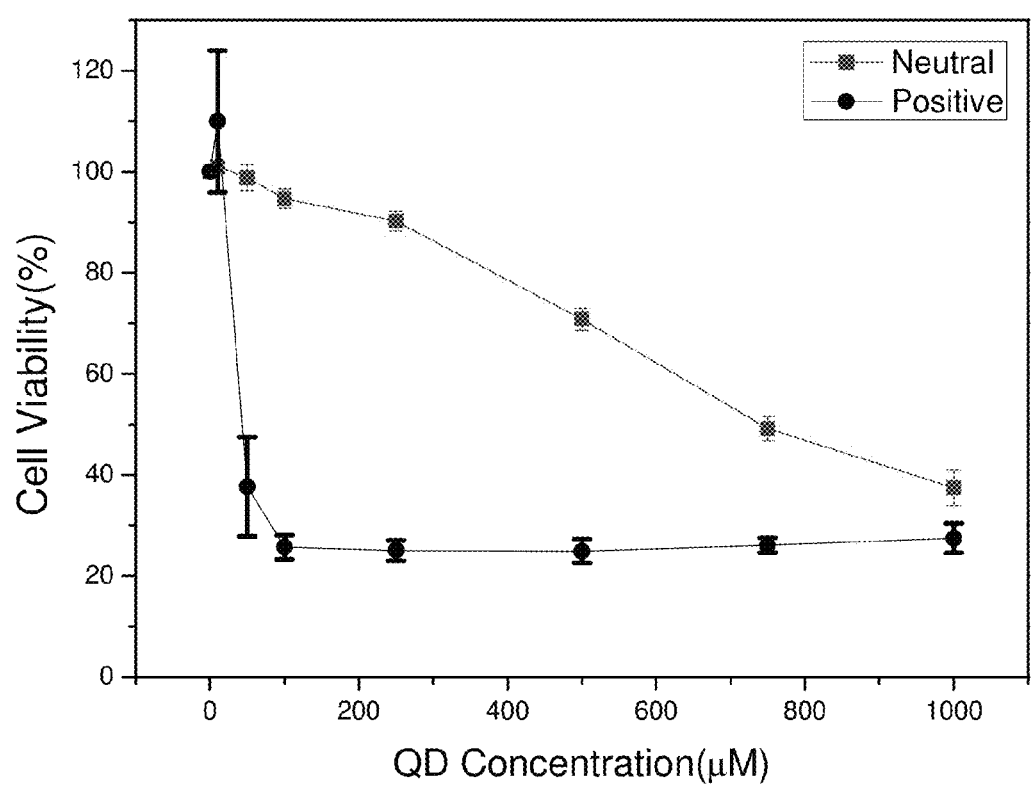
FIG. 5A plots the cell viability as a function of QD concentration for a 3T3 cell line for positively charged Cys-SnS and neutral MPA-modified SnS at 24 hours.

After 24 hours, the above-described cytotoxicity test indicated that only about 20% of cells were when the QD concentration was higher than 100 µM for SnS QDs without surface modification. The high toxicity shown in FIG. 5A was attributed to the positive charge on the QDs since positively charged particles can enter cells through endocytosis.

Figure 5B:
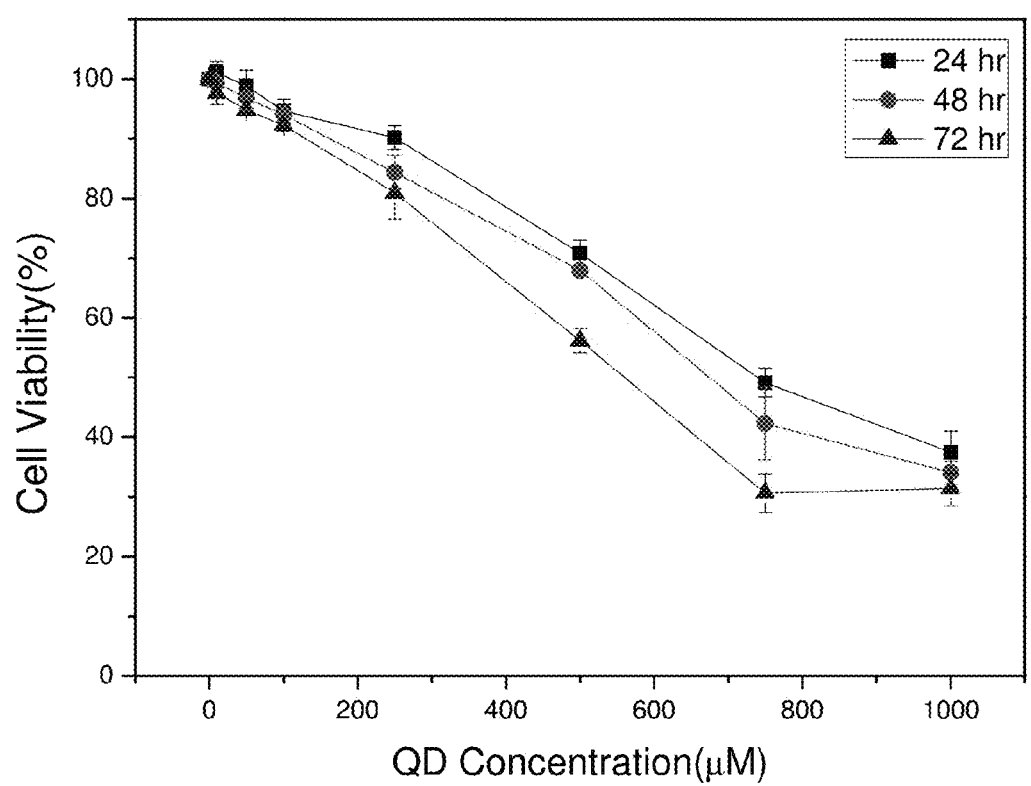
FIG. 5B plots the cell viability as a function of QD concentration for a 3T3 cell line for neutral MPA-modified SnS at 24, 48, and 72 hours.

To reduce cytotoxicity, negatively charged MPA was added to the suspension to react with the Cys to neutralize the positive charge from 32 mV to 1.3 mV. FIG. 5B shows that cells incubated with the MPA-modified SnS QDs showed an increase in cell viability. The $LD_{50}$ for the MPA-modified SnS QDs was found to be 500 µM after 72 hrs. incubation. The concentration used in the immunofluorescent staining study was 80 µM, which is much lower than the $LD_{50}$ concentration.

Figure 6:
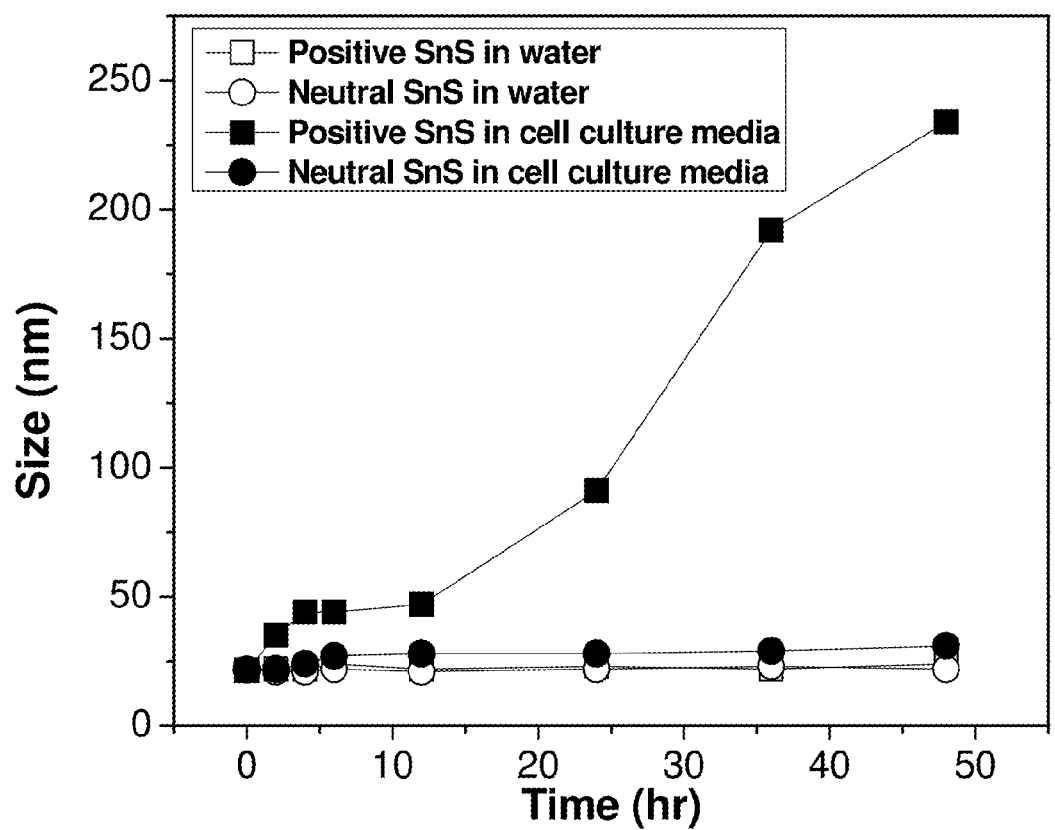
FIG. 6 plots the stability of positively charged Cys-SnS and neutral MPA-modified SnS in water and cell culture media.

MPA neutralization of the QD surface charge also plays an important role in the stability of the SnS QDs in cell culture. FIG. 6 shows the stability of the SnS QDs in water and in cell culture. Although positively charged SnS QDs are stable in water, they are not stable in cell culture medium. However, as shown in FIG. 6, after adding MPA to neutralize the surface charge, the SnS QDs became stable in culture medium.

Figure 7A:
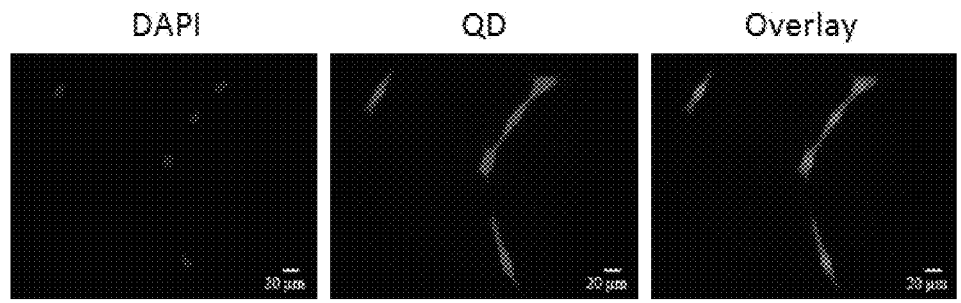
FIG. 7A shows fluorescence images of 3T3 cells with streptavidin (SA)-SnS QDs with an antibody.
Figure 7B:
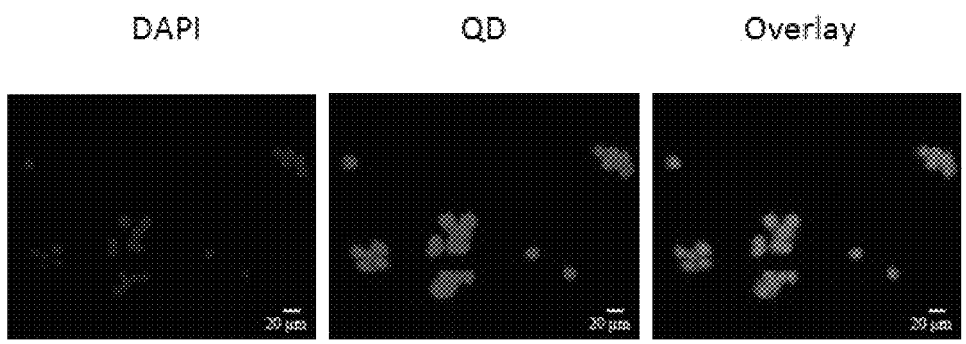
FIG. 7B shows fluorescence images of HT29 stained with SA-SnS QDs with an antibody.
Figure 7C:
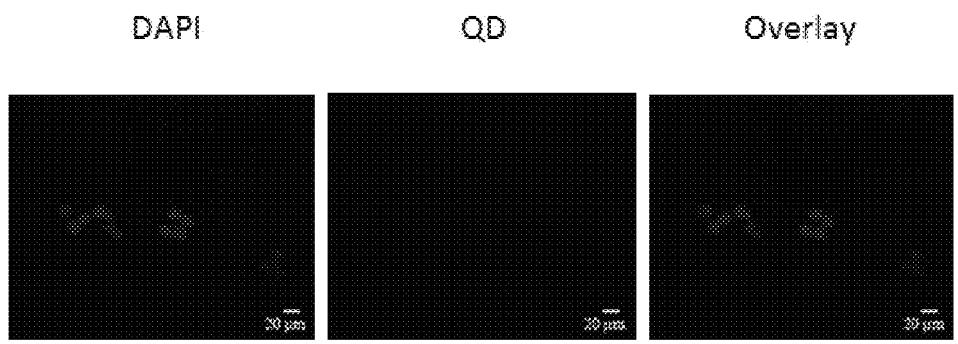
FIG. 7C shows fluorescence images of HT29 stained SA-SnS QDs but without the antibody, which serves as a negative control for FIG. 7B.

The imaging capability of the SnS QDs was studied using the fibroblast cell line 3T3 and the cancer cell line HT29. It has been shown previously that Tn-antigen was present on the surface of HT29. Au, G. H., et al., 2012, *International journal of surgical oncology* 2012. Therefore, SA-SnS QDs were used to stain the biotinylated secondary antibodies that were linked to the primary antibodies bound to Tn-antigen on HT29 through the streptavidin-biotin linkage as shown in FIG. 7B. The control group, which employed HT29 cells stained with QDs without primary antibody during immunofluorescent staining, is shown in FIG. 7C. There is no QDs signal in FIG. 7C, meaning that non-specific binding is well prevented. The 3T3 cell line was also stained with SA-SnS QDs with the antibody and the results are shown in FIG. 7A. A DAPI image, a QD fluorescence image, and the overlay of both of the 3T3 and HT29 cells treated with the SA-SnS QD mixture at a SA/QD ratio of 22:1 are shown in FIGS. 7A-7B, respectively. The bright red QD signal in FIG. 7B indicates detection of Tn antigen on HT29 cells. All cell membranes are uniformly stained by the QDs, indicating that the SA conjugated QDs are capable of imaging cell membranes. In FIGS. 7A-7C, the first, second, and third columns show the images of DAPI staining, SA-QDs staining, and an overlay of the DAPI staining and the SA-QDs staining, respectively.

Figure 8A:
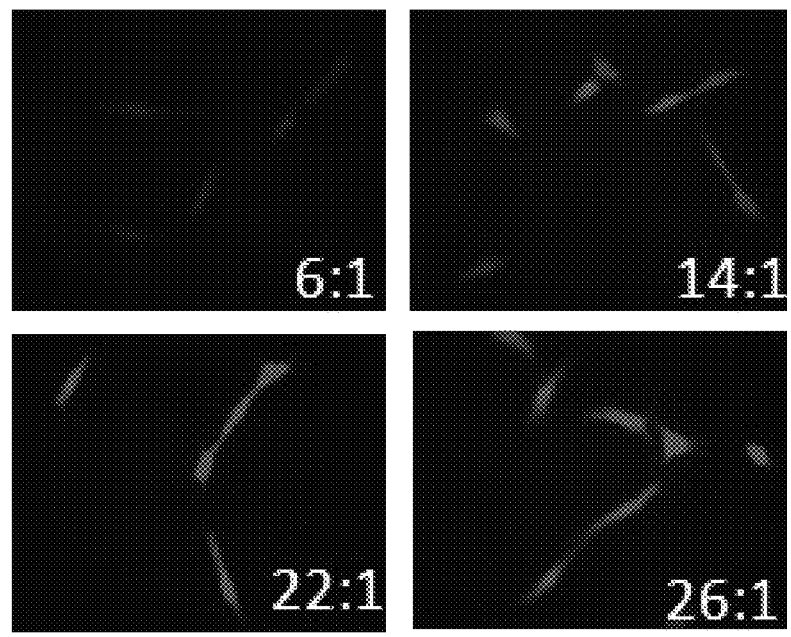
FIG. 8A shows fluorescence images of 3T3 cells stained with SnS QDs with SA:QD ratios of 6:1, 14:1, 22:1, and 26:1.
Figure 8B:
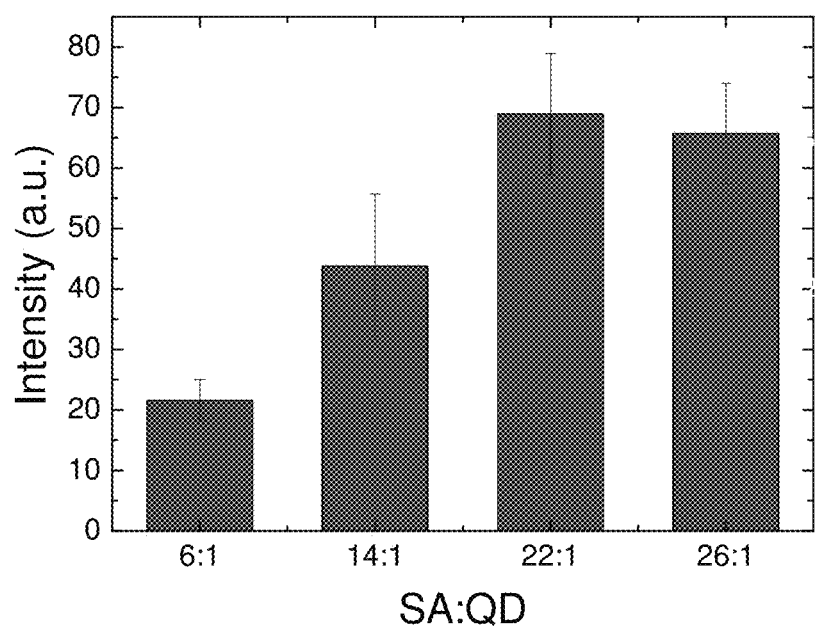
FIG. 8B shows an analysis of the average QD intensity on each cell for 3T3 cells stained with the different SA:QD ratios shown in FIG. 8A.

The amount of SA and its effects on staining was also studied by changing the SA/QD ratio from 6:1 to 26:1. The fluorescence images of 3T3 cells stained with SnS QDs with SA/QD ratios of 6:1, 14:1, 22:1, and 26:1, respectively are shown in FIG. 8A. FIG. 8B shows an analysis of the average QD signal intensity on each cell after immunofluorescence staining. The SA/QD ratio of 22:1 resulted in the maximum intensity. This SA/QD ratio of 22:1 was the ratio used in the cancer cell line HT29 staining shown in FIGS. 7B-7C.

Figure 17:
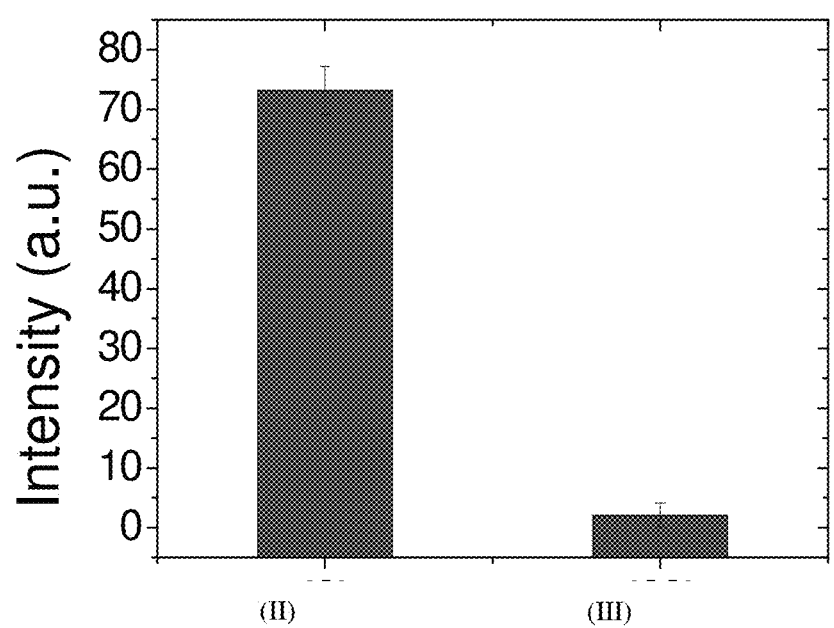
FIG. 17 shows SnS QD signal intensity per unit area of HT29 cells stained with SnS QD (II) and the negative control (III), of FIGS. 7A-7C.

The imaging capability of the SnS QDs for cancer cell line HT29 was also studied. FIG. 17 shows the QD signal intensity per unit area of HT29 cells after staining (II) and for the negative control (III). The ratio of QD signal intensity after staining (II) to the signal intensity of the negative control (III) was calculated to be 35, which gives the signal to noise ratio of SnS/QDs staining of Tn antigen on HT 29 cells. Cysteamine-capped SnS QDs were successfully synthesized in glycerol followed by capping molecule extending with glycine via peptide formation. It was shown that SnS QDs exhibited an NIR emission with a peak emission wavelength of 830 nm. The surface-modified SnS QDs exhibited excellent stability with low cytotoxicity. The imaging capability of the SnS QDs was also demonstrated by immunofluorescent staining on cancer cell membranes.

Example 7

Cation-Inverting-Injection Method

After stabilization of the SnS QDs by extending the capping molecules as discussed above, hydrothermal treatment was needed to improve the PL intensity. However, for the hydrothermal treatment, the large amount of water added during glycine extending process has to be replaced by solvent exchange with glycerol to avoid the limitation of boiling of water at 100° C. In the examples described above, it was necessary to increase the percentage of glycerol from 60% to 99% before hydrothermal treatment. The solvent exchange process using centrifugation is very tedious due to the high viscosity of glycerol. In addition, the yield was very low since high temperature treatment can cause aggregation. Consequently, the above-described synthesis was modified as described below.

To avoid the tedious solvent exchange process and hydrothermal treatment with low yield, a cation-inverting-injection synthesis method was employed to improve the PL intensity of the SnS QDs. It is believed that the cation-inverting-injection increases the edge-state emission and suppresses the trap-state emission. Also the lower cation concentration that results in this method allows more anions to participate in the growth of the QDs. As shown in FIGS. 9A-9B, use of a low Sn concentration during the gradual addition of the $Sn^{2+}$ ions leads to the formation of only a few SnS nuclei, leaving most of the $S^{2-}$ ions available for QD growth.

In the process of FIG. 9A, $S^{2-}$ ions were added into glycerol, the pH was adjusted to 3 and then cysteamine was added. In the process of FIG. 9B $Sn^{2+}$ ions and cysteamine were added at pH 3, the pH having been adjusted using nitric acid. After 10 minutes, the solution of FIG. 9B was slowly pumped into the solution of FIG. 9A.

It was found that this cation-inverting-injection synthesis method increased the PL intensity from 140,000 to 450,000, without the need for heat treatment. Further, extending of the capping molecules of these SnS QDs using glycine, as described above, provided an SNS QD suspension that was stable for at least one week at pH 6.5.

Example 8

Cation-Inverting Method

Based on a ratio of Cys:Sn:S=16:7:1), a ratio of Cys:S is 8:7, a ratio of Cys:Sn is 8:7 in solution B. In beaker A, add 1 ml of S into 17 ml of glycerol with 5 min stirring. Adjust pH to 3 by adding nitric acid followed by 5 minutes of stirring. Add 2 ml of cysteamine precursor solution, followed by 10 min of stirring. At the meantime, in beaker B, add 28 ml Sn precursor into 10 ml of glycerol and stir for 5 mins. Then add 2 ml of cysteamine into beaker B and stir for 5 mins. As the pre-reaction in two beakers is completed, start to slowly drop solution B into beaker A by pumping. The hot plate starts to gradually heat up to a different temperature as the dropping starts. Stir for 1.5 hours and store it in a 4° C. refrigerator. The final concentration of SnS suspension is 1.3 mM based on the concentration of S. The molecular ratio of cysteamine:Sn:S is 16:7:1.

Figure 13:
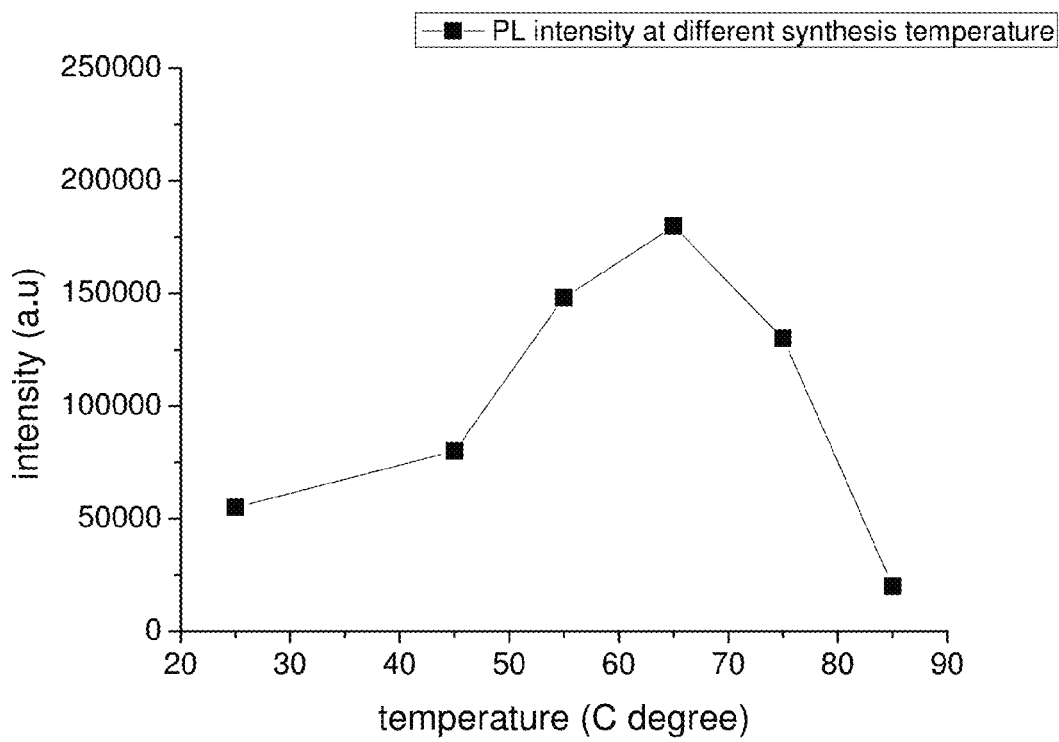
FIG. 13 shows the PL intensity of SnS QDs made at different temperatures.
Figure 14:
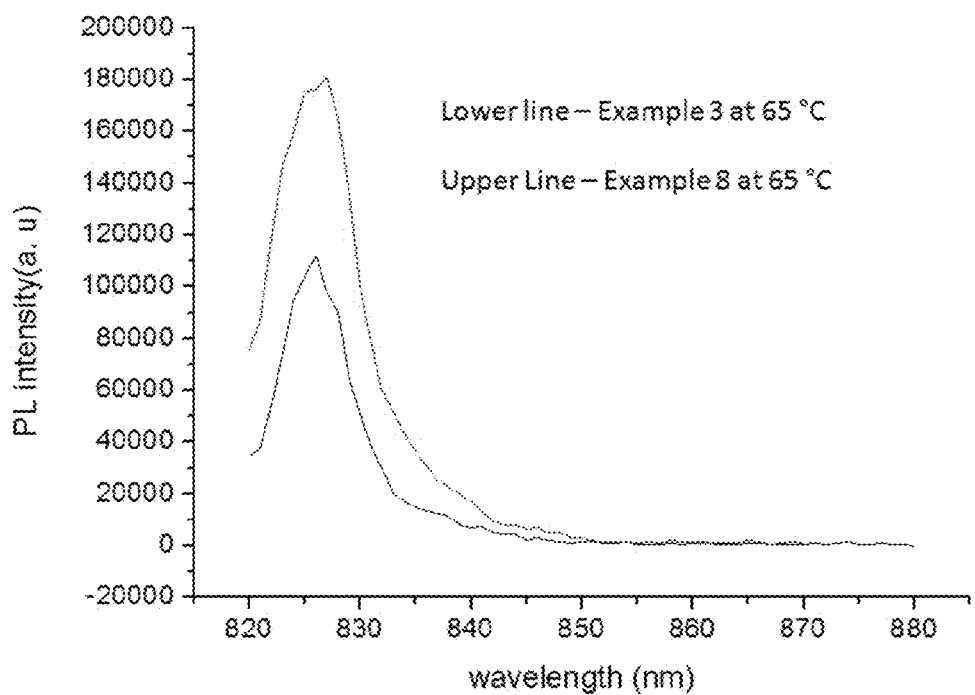
FIG. 14 shows a comparison of the PL intensity of SnS QDs made by Examples 3 and 8 at 65° C.

As shown in FIG. 13, 65° C. was found to be the optimal temperature, and the PL intensity was increased about 130% compared to Example 7 by changing the molecular ratio (FIG. 14).

Example 9

Varying Molecular Ratios

Figure 15:
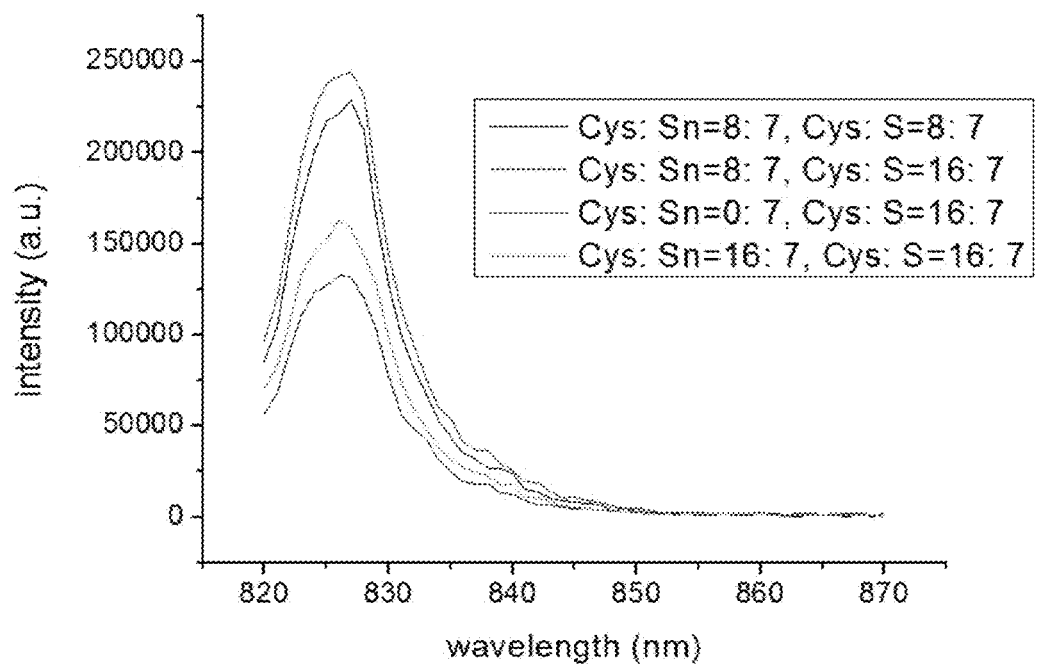
FIG. 15 shows the effect of molecular ratio on the PL intensity.

Different molecular ratios were studied and ratio of Cysteamine:Sn:S=24:7:1 has highest PL intensity with Cys:S=16:1 for solution A and Cys:Sn=8:7 for solution B respectively (FIG. 15).

The foregoing examples have been presented for the purpose of illustration and description only and are not to be construed as limiting the invention in any way. The scope of the invention is to be determined from the claims appended hereto.

Other embodiments of the present disclosure will be apparent to those skilled in the art from consideration of the specification and practice of the embodiments disclosed herein. It is intended that the specification and examples be considered as exemplary only, with a true scope of the disclosure being indicated by the following claims.

All documents mentioned herein are hereby incorporated by reference in their entirety or alternatively to provide the disclosure for which they were specifically relied upon.

The applicant(s) do not intend to dedicate any disclosed embodiments to the public, and to the extent any disclosed modifications or alterations may not literally fall within the scope of the claims, they are considered to be part hereof under the doctrine of equivalents.

The invention claimed is:

1. A method for the preparation of tin sulfide quantum dots that exhibit a near infrared emission for use in in vivo imaging comprising steps of:
 (a) reacting $Sn^{2+}$ cations with $S^{2-}$ anions in water, a water-miscible solvent or a combination thereof and a capping molecule to form capped SnS quantum dots by
  (i) providing a solution of capping molecule at a pH of from about 1 to about 7 and a temperature of from about 50-90° C.;
  (ii) adding a precursor solution containing $Sn^{2+}$ cations while maintaining the temperature at from about 50-90° C. and maintaining the pH at from about 1 to about 7 to provide a mixture; and
  (iii) adding an aqueous precursor solution containing $S^{2-}$ anions to the mixture while maintaining the temperature at from about 50-90° C. and maintaining the pH at from about 1 to about 7;
 (b) optionally extending at least some of the capping moieties of the SnS quantum dots by peptide bond formation to provide extended capped SnS quantum dots; and
 (c) if necessary, neutralizing the extended capped SnS quantum dots, and
 (d) heat treating the extended capped SnS quantum dots to increase a photoluminescence intensity of the quantum dots; and
wherein the molar ratio of capping molecule:S in the quantum dots is from about 8.1 to about 32:1 and the molar ratio of Sn:S in the quantum dots is from about 3:1 to about 12:1.

2. The method as claimed in claim 1, wherein the molar ratio of capping molecule:S in the quantum dots is from about 12:1 to about 20:1.

3. The method as claimed in claim 1, wherein the heat treating step is carried out at a temperature of from about 180° C. to about 220° C.

4. The method as claimed in claim 1, wherein the heat treating step is carried out for a time of from about 0.25 to 5 hours.

5. The method as claimed in claim 1, wherein the process includes the extending step (b), glycine is employed in the extending step (b), cysteamine is employed as the capping molecule and a glycine to cysteamine molar ratio used to extend the capping molecule is from about 3 to about 30.

6. The method of claim 5, wherein step (c) is performed and 3-mercaptopropionic acid is employed in step (c) to neutralize the SnS quantum dot.

7. A method for the preparation of tin sulfide quantum dots that exhibit a near infrared emission for use in in vivo imaging comprising steps of:
 (a) reacting $Sn^{2+}$ cations with $S^{2-}$ anions in water, a water-miscible solvent or a combination thereof and a capping molecule to form capped SnS quantum dots by
  (i) providing a solution containing $S^{2-}$ ions at a pH of from about 1 to about 7,
  (ii) adding capping molecules to the solution containing $S^{2-}$ ions while maintaining the pH at from about 1 to about 7 to provide a solution containing capping molecules and $S^{2-}$ ions;
  (iii) slowly adding a solution containing $Sn^{2+}$ ions at a pH of from about 1 to about 7 to the solution containing capping molecules and $S^{2-}$ ions
 (b) optionally extending at least some of the capping moieties of the SnS quantum dots by peptide bond formation to provide extended capped SnS quantum dots; and (c) if necessary, neutralizing the extended capped SnS quantum dots, and wherein the molar ratio of capping molecule:S in the quantum dots is from about 8:1 to about 32:1.

8. The method as claimed in claim 7, wherein the molar ratio of capping molecule:S in the quantum dots is from about 12:1 to about 20:1.

9. The method as claimed in claim 7, wherein the molar ratio of Sn:S in the quantum dots is from about 1:1 to about 32:1.

10. A method for the preparation of tin sulfide quantum dots that exhibit a near infrared emission for use in in vivo imaging comprising steps of:
(a) reacting $Sn^{2+}$ cations with $S^{2-}$ anions in water, a water-miscible solvent or a combination thereof and a capping molecule to form capped SnS quantum dots by
  (i) providing a solution containing $S^{2-}$ ions at a pH of from about 1 to about 7,
  (ii) adding capping molecules to the solution containing $S^{2-}$ ions while maintaining the pH at from about 1 to about 7 to provide a solution containing capping molecules and $S^{2-}$ ions;
  (iii) slowly adding a solution containing $Sn^{2+}$ ions at a pH of from about 1 to about 7 to the solution containing capping molecules and $S^{2-}$ ions
(b) optionally extending at least some of the capping moieties of the SnS quantum dots by peptide bond formation to provide extended capped SnS quantum dots, and
(c) if necessary, neutralizing the extended capped SnS quantum dots, and wherein the molar ratio of Sn:S in the quantum dots is from about 3:1 to about 12:1.

11. A method for the preparation of tin sulfide quantum dots that exhibit a near infrared emission for use in in vivo imaging comprising steps of:
(a) reacting $Sn^{2+}$ cations with $S^{2-}$ anions in water, a water-miscible solvent or a combination thereof and a capping molecule to form capped SnS quantum dots by
  (i) providing a solution containing $S^{2-}$ ions at a pH of from about 1 to about 7,
  (ii) adding capping molecules to the solution containing $S^{2-}$ ions while maintaining the pH at from about 1 to about 7 to provide a solution containing capping molecules and $S^{2-}$ ions;
  (iii) slowly adding a solution containing $Sn^{2+}$ ions at a pH of from about 1 to about 7 to the solution containing capping molecules and $S^{2-}$ ions
(b) extending at least some of the capping moieties of the SnS quantum dots by peptide bond formation to provide extended capped SnS quantum dots; and
(c) if necessary, neutralizing the extended capped SnS quantum dots; and wherein glycine is employed in the extending step (b), cysteamine is employed as the capping molecule and a glycine to cysteamine molar ratio used to extend the capping molecule is from about 3 to about 30.

12. The method of claim 11, wherein step (c) is performed and 3-mercaptopropionic acid is employed in step (c) to neutralize the SnS quantum dot.

13. The method as claimed in claim 1, wherein the heat treating step is carried out at a temperature of from about 190° C. to about 220° C., for a time of from about 0.5 to 4 hours and wherein the process includes the extending step (b), glycine is employed in the extending step (b), cysteamine is employed as the capping molecule and a glycine to cysteamine molar ratio used to extend the capping molecule is from about 10 to about 20.

14. The method as claimed in claim 11, wherein the glycine to cysteamine molar ratio used to extend the capping molecule is from about 10 to about 20.

15. The method of claim 14, wherein step (c) is performed and 3-mercaptopropionic acid is employed in step (c) to neutralize the SnS quantum dot.

16. The method as claimed in claim 10, wherein the molar ratio of capping molecule:S in the quantum dots is from about 8:1 to about 32:1.

17. The method as claimed in claim 10, wherein the molar ratio of capping molecule:S in the quantum dots is from about 12:1 to about 20:1.

18. The method as claimed in claim 11, wherein the molar ratio of capping molecule:S in the quantum dots is from about 12:1 to about 20:1.

19. The method as claimed in claim 11, wherein the molar ratio of Sn:S in the quantum dots is from about 1:1 to about 32:1.

* * * * *